United States Patent
Head et al.

[19]

[11] Patent Number: 6,142,147
[45] Date of Patent: Nov. 7, 2000

[54] NASAL DELIVERY SYSTEM FOR INHALED NITRIC OXIDE

[75] Inventors: C. Alvin Head, Winchester; Dean R. Hess, Danvers, both of Mass.

[73] Assignee: The General Hospital Corporation, Boston, Mass.

[21] Appl. No.: 09/064,123

[22] Filed: Apr. 21, 1998

Related U.S. Application Data

[60] Provisional application No. 60/080,048, Mar. 31, 1998.

[51] Int. Cl.[7] .............................. A61M 16/00; A62B 7/00; F16K 31/02
[52] U.S. Cl. .............................. 128/204.21; 128/203.12; 128/204.18; 128/204.23; 128/204.26
[58] Field of Search .................. 128/203.12, 204.18, 128/204.21, 204.23, 204.26, 205.26, 205.24

[56] References Cited

U.S. PATENT DOCUMENTS

| | | | |
|---|---|---|---|
| 3,653,401 | 4/1972 | Beeler et al. | 137/355.17 |
| 3,965,903 | 6/1976 | Cranage | 128/200.14 |
| 3,970,103 | 7/1976 | McKee | 137/357 |
| 4,420,013 | 12/1983 | DiBlasio | 137/382 |
| 4,457,303 | 7/1984 | Durkan | 128/204.24 |
| 4,462,398 | 7/1984 | Durkan et al. | 128/200.14 |
| 4,484,578 | 11/1984 | Durkan | 128/204.24 |
| 4,519,387 | 5/1985 | Durkan et al. | 128/204.23 |
| 4,527,587 | 7/1985 | Fairlamb | 137/329.3 |
| 4,886,055 | 12/1989 | Hoppough | 128/200.14 |
| 4,991,820 | 2/1991 | Kohn et al. | 251/149.5 |
| 5,485,827 | 1/1996 | Zapol et al. | 128/200.14 |
| 5,485,833 | 1/1996 | Dietz | 128/204.23 |
| 5,522,381 | 6/1996 | Olsson et al. | 128/203.12 |
| 5,531,218 | 7/1996 | Krebs | 128/203.12 |
| 5,558,083 | 9/1996 | Bathe et al. | 128/203.12 |
| 5,615,669 | 4/1997 | Olsson et al. | 128/203.12 |
| 5,651,358 | 7/1997 | Briend et al. | 128/203.12 |
| 5,701,883 | 12/1997 | Hete et al. | 128/204.26 |
| 5,713,349 | 2/1998 | Keaney | 128/204.23 |
| 5,732,693 | 3/1998 | Bathe et al. | 128/203.12 |
| 5,732,694 | 3/1998 | Bathe et al. | 128/203.12 |
| 5,752,506 | 5/1998 | Richardson | 128/204.18 |
| 5,839,433 | 11/1998 | Higenbottam | 128/204.21 |
| 5,871,009 | 2/1999 | Rydgren et al. | 128/203.12 |
| 5,918,596 | 7/1999 | Heinonen | 128/204.21 |
| 6,016,801 | 1/2000 | Philips | 128/203.12 |

FOREIGN PATENT DOCUMENTS

| | | | |
|---|---|---|---|
| WO 95/10315 | 4/1995 | WIPO | A61M 16/00 |
| WO 97/31670 | 9/1997 | WIPO | 128/204.23 |

OTHER PUBLICATIONS

Bower et al., "Performance of a Demand Oxygen Saver System During Rest, Exercise, and Sleep in Hypoxemic Patients", Chest 94:77–80, 1988.

(List continued on next page.)

*Primary Examiner*—John G. Weiss
*Assistant Examiner*—Joseph F. Weiss, Jr.
*Attorney, Agent, or Firm*—Fish & Richardson P.C.

[57] ABSTRACT

A device for pulsed delivery of inhaled nitric oxide (NO) to a spontaneously breathing patient is disclosed. The device delivers NO, e.g., through a nasal cannula, only during the inspiratory phase of the breathing cycle. The device automatically executes a purge cycle when it is initially activated, and when the time between breath-triggered NO pulses reaches a predetermined time limit. The purge cycle protects the patient from exposure to $NO_2$ that otherwise would accumulate in the fluid lines from the reaction of static NO with oxygen in the air.

8 Claims, 5 Drawing Sheets

OTHER PUBLICATIONS

Branson, "The Nuts and Bolts of Increasing Arterial Oxygenation: Devices and Techniques", *Respiratory Care* 38:672–686, 1993.

Braun et al., "Comparison of Six Oxygen Delivery Systems for COPD Patients at Rest and During Exercise", *Chest* 102:694–698, 1992.

Carter et al., "Demand Oxygen Delivery for Patients with Restrictive Lung Disease", *Chest* 96:1307–1311, 1989.

DeVilbiss EX2000D Pulse Dose® Conserving Device Instruction Guide, Important Parts of Your PulseDose Conserving Device, 2 pages.

Hess et al., "Delivery Systems for Inhaled Nitric Oxide", *Respiratory Care Clinics of North American* 3:371–410, 1997.

Hoffman, "Novel Strategies for Delivering Oxygen: Reservoir Cannula, Demand Flow, and Transtracheal Oxygen Administration", *Respiratory Care* 39:363–377, 1994.

Kerby et al., "Clinical Efficacy and Cost Benefit of Pulse Flow Oxygen in Hospitalized Patients", *Chest* 97:379–372, 1990.

McDonnell et al., "Efficacy of Pulsed Oxygen Delivery During Exercise", *Respiratory Care* 31:883–888, 1986.

Mecikalski et al., "A Demand Valve Conserves Oxygen in Subjects with Chronic Obstructive Pulmonary Disease", *Chest* 86:667–670, 1984.

Sato et al., "Evaluation of the Ability of the Syncoxy Breath–Synchronized Valve to Provide Adequate Oxygen Levels", *Respiratory Care* 37:869–876, 1992.

Senn et al., "Efficacy of a Pulsed Oxygen Delivery Device During Exercise in Patients with Chronic Respiratory Disease", *Chest* 96:467–472, 1989.

Tiep et al., "Demand Oxygen Delivery During Exercise", *Chest* 91:15–20, 1987.

Tiep et al., "Low–concentration Oxygen Therapy Via a Demand Oxygen Delivery System", *Chest* 87:636–638, 1985.

Tiep et al., "Pulsed Nasal and Transtracheal Oxygen Delivery", *Chest* 97:364–368, 1990.

Yuan et al., "Clinical Evaluation of Pulse–Dose and Continuous–Flow Oxygen Delivery", *Respiratory Care* 40:811–814, 1995.

NASAL DELIVERY SYSTEM FOR INHALED NITRIC OXIDE

CROSS REFERENCE TO RELATED APPLICATION

This application claims benefit from provisional application Serial No. 60/080,048 filed Mar. 31, 1998.

BACKGROUND OF THE INVENTION

There is growing interest in the use of inhaled nitric oxide (NO) to treat various conditions characterized by pulmonary hypertension or hypoxemia. Clinical use of inhaled NO began in the early 1990s. To date, inhaled NO has been administered primarily to critically ill, intubated, mechanically ventilated patients. Recently, it has become recognized that inhaled NO is also useful for treatment of spontaneously breathing patients such as cardiac surgery patients, organ transplant patients, and patients with pulmonary hypertension or sickle cell disease.

Systems for delivering inhaled NO to spontaneously breathing patients have been described (Wessel et al., 1994, *Crit. Care. Med.* 22:930). Inhaled NO has been delivered to spontaneously breathing patients through a nasal cannula (Yoshida et al., 1997, *Am. J. Respir. Crit. Care Med.* 155:526). In some cases, NO delivery through a nasal cannula has been pulsed delivery (Channick et al., 1996, *Chest* 109:1545).

In a normal human breathing pattern, about one third of the time consists of inspiration (inhalation), and about two thirds of the time consists of expiration (exhalation). Thus, in a continuous flow nasal cannula system, at least two thirds of the gas flowing from the source, e.g., a portable gas cylinder, is wasted. The basic concept of a pulsed dosage system is to deliver the therapeutic gas, e.g., oxygen or NO, only during the inspiratory phase of the breathing cycle.

By conserving gas, a pulsed dosage system reduces NO costs. It also increases the lifetime of an No source (gas cylinder), or decreases cylinder size. The latter two considerations are particularly important in home-care systems and portable systems for ambulatory patients. The mixture of NO and nitrogen administered from a nasal cannula system contains no moisture, and can cause discomfort from a drying effect on nasal membrane tissue. Thus, an additional benefit of a pulsed dosage system is reduced drying of nasal tissues. This increases patient comfort and improves patient compliance.

NO is an unstable, diatomic, highly lipophilic free radical. NO reacts rapidly with molecular oxygen ($O_2$) to produce nitrogen dioxide ($NO_2$), which is toxic at low levels. OSHA has set exposure limits for $NO_2$ at 5 ppm. Animal studies have shown altered surfactant hysteresis and produced alveolar cell hyperplasia, changes in the epithelium of the terminal bronchiole, and loss of cilia at inhaled $NO_2$ concentrations as low as 2 ppm (Evans et al., 1972, *Arch. Environ. Health* 24:180; Stephens et al., 1972, *Arch. Environ. Health* 24:160. In humans, 2.3 ppm $NO_2$ has been shown to affect alveolar permeability (Rasmussen et al., 1992, *Am. Rev. Respir. Dis.* 146:654). Increased airway reactivity in humans has been found at inhaled $NO_2$ concentrations below 2 ppm (Bylin et al., 1988, *Eur. Respir. J.* 1:606; Morrow et al., 1992, *Am. Rev. Respir. Dis.* 145:291; Stephens et al., supra).

NO is typically manufactured from the reaction of sulfur dioxide with nitric acid (Body et al., 1995, *J. Cardiothorac. Vasc. Anesth.* 9:748). Alternatively, it can be produced by reacting sodium nitrite and sulfuric acid (Young et al., 1996, *Intensive Care Med.* 22:77) or by the oxidation of ammonia over a platinum catalyst at high temperatures (Body et al., supra). Following its production, NO is mixed with nitrogen gas ($N_2$) to obtain the desired NO concentration. The $NO/N_2$ mixture is placed into specially prepared, aluminum alloy cylinders. For medical applications, cylinders typically contain 400 to 800 ppm NO (Hess et al., supra). In an NO cylinder, the $NO_2$ concentration is normally less than 2% of the NO concentration.

SUMMARY OF THE INVENTION

The invention features a device for pulsed delivery of inhaled nitric oxide to a spontaneously breathing patient. The device includes a valve having a first, a second, and a third port. The first port is selectively communicable with the second port or the third port. The device also includes a pressure sensor in fluid communication with the third port. A valve controller is responsive to the pressure sensor. The valve controller selectively connects the first port to the to the second port when a negative pressure event is sensed, maintains the connection for at least a portion of the negative pressure event duration, and reconnects the first port to the third port after a predetermined pulse time. A monitor operably linked to the valve controller measures the duration of connection between the first port and third port, and signals the valve controller to selectively connect the first port to the second port for a predetermined purge time when the duration of connection between the first port and third port exceeds a predetermined flow-off time, and then signals the valve controller to reconnect the first port to the third port. The monitor and automatic purge cycle advantageously protect the patient from exposure to $NO_2$ which otherwise would accumulate in fluid lines during an extended period in which NO/nitrogen does not flow.

The device can include a means for inactivation when not in use, e.g., an on/off switch, and a means for triggering the valve controller to selectively connect the first port to the second port for a predetermined purge time whenever the device undergoes start-up following a state of inactivation. This feature advantageously protects the patient from exposure to $NO_2$ accumulated in the fluid lines, when the patient initiates use of the device after the device has been turned off.

The purge time is preselected to provide a purge volume of 1 to 5 dead space volumes, preferably from 2 to 4 dead space volumes, and most preferably about 3 dead space volumes.

The device can also include an alarm operably connected to the monitor. The alarm provides a visual or audible indication whenever the duration of connection between the first port and third port exceeds a predetermined flow-off time, i.e., when the pressure sensor fails to detect inspiration by the patient. The alarm alerts the patient and/or a caretaker that pulsatile delivery of NO has not occurred for a preselected time, e.g., 15 seconds, 30 seconds, or 45 seconds.

The device can also include a purge cycle indicator that provides a continuous visual or audible indication that begins whenever a purge cycle begins, continues throughout the purge cycle, and ends when the purge cycle ends. This indicator warns the patient or caretaker when to wait for $NO_2$ to be purged from the system, and when it is safe to begin use of the device.

The invention also includes a dual delivery device for separate, concurrent, pulsed delivery of inhaled nitric oxide and pulsed delivery of oxygen through a split nasal cannula to a spontaneously breathing patient. NO is delivered through one side of the split cannula, and oxygen is delivered independently through the other side of the split cannula.

The NO portion of the dual delivery device includes a valve having a first, a second, and a third port. The first port is selectively communicable with the second port or the third port. The NO portion of the device also includes a pressure sensor in fluid communication with the third port, and a valve controller responsive to the pressure sensor. The valve controller selectively connects the first port to the to the second port when a negative pressure event is sensed, maintains the connection for at least a portion of the negative pressure event duration, and reconnects the first port to the third port after a predetermined NO pulse time. A monitor operably linked to the valve controller measures the duration of connection between the first port and third port, and signals the valve controller to selectively connect the first port to the second port for a predetermined purge time when the duration of connection between the first port and third port exceeds a predetermined flow-off time. The monitor then signals the valve controller to reconnect the first port to the third port.

The dual delivery device also includes a pulsed oxygen delivery system that includes a valve having a first, a second, and a third port. The first port is selectively communicable with the second port or the third port. The oxygen portion of the dual delivery device also includes a pressure sensor in fluid communication with the third port, and a valve controller responsive to the pressure sensor. The valve controller selectively connects the first port to the to the second port when a negative pressure event is sensed, maintains the connection for at least a portion of the negative pressure event duration, and reconnects the first port to the third port after a predetermined oxygen pulse time.

The oxygen portion of the dual delivery device can also include a monitor operably linked to the valve controller. The monitor measures the duration of connection between the first port and third port; and an alarm indicator operably linked to the monitor so that an oxygen pulse "fail" alarm indication results when the monitor detects a duration of connection between the first port and third port equal to, or greater than a predetermined time limit. This feature alerts the patient or caregiver that the desired pulsed oxygen delivery is not taking place on the oxygen side of the system.

Unless otherwise defined, all technical and scientific terms used herein have the same meaning as commonly understood by one of ordinary skill in the art to which this invention belongs. In case of conflict, the present application, including definitions will control. All publications, patent applications, patents, and other references mentioned herein are incorporated by reference.

Although methods and materials similar or equivalent to those described herein can be used in the practice or testing of the present invention, the preferred methods and materials are described below. The materials, methods, and examples are illustrative only and not intended to be limiting. Other features and advantages of the invention will be apparent from the detailed description, and from the claims.

DETAILED DESCRIPTION

Figure 1:
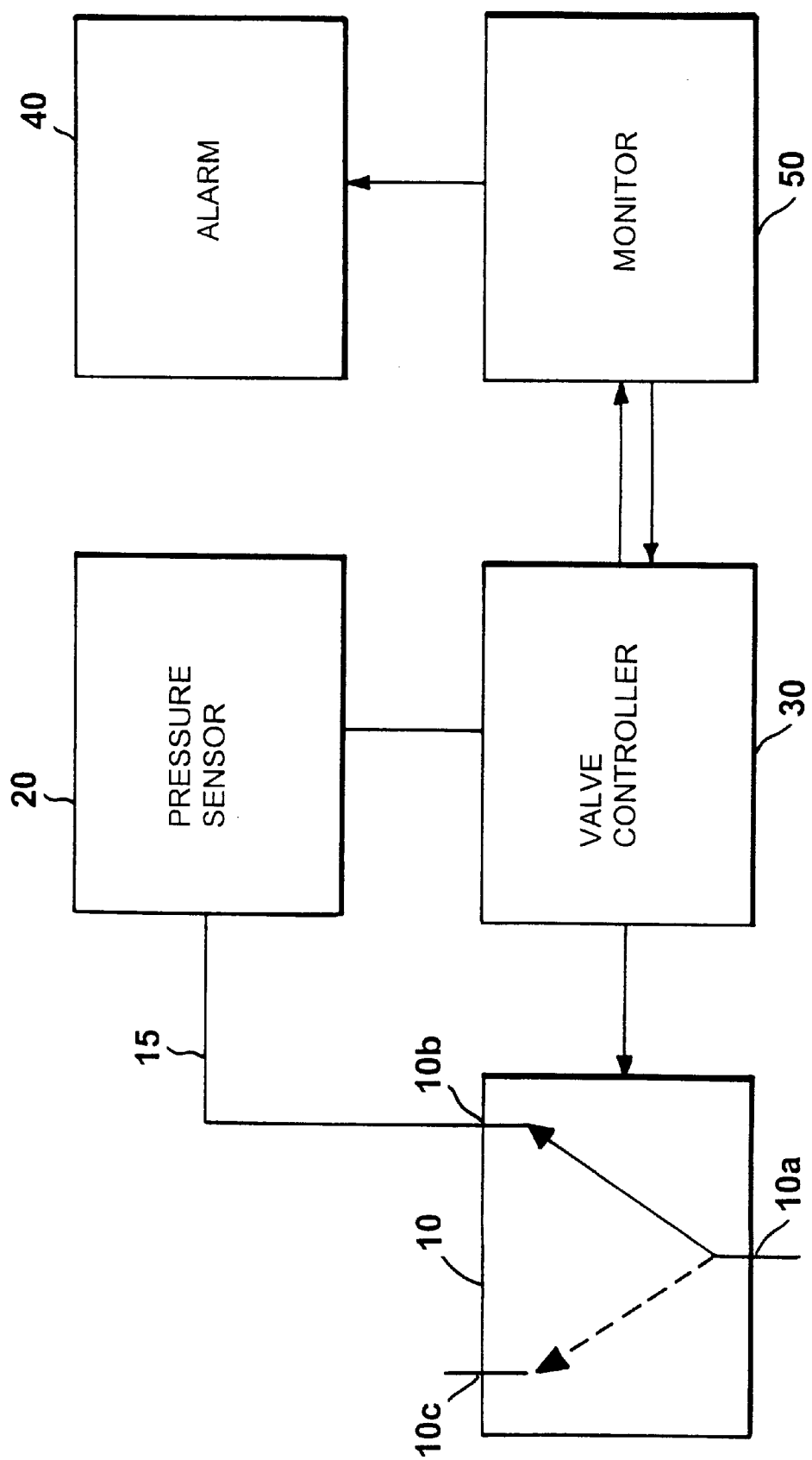
FIG. 1 is a block diagram showing the arrangement of a valve, valve controller, pressure sensor, monitor, and alarm, in a device according to the invention.

An embodiment of the invention represented schematically in FIG. 1 includes a three-way, two position valve 10, such as a solenoid-actuated, spool valve. Valve 10 has ports 10a, 10b, and 10c in its bore. Port 10a is connected to a line (not shown) so as to be in fluid communication with a nasal cannula (not shown). Port 10c is connected to a line (not shown) so as to be in fluid communication with a source of NO gas (not shown). Port 10b is in fluid communication with a pressure sensor 20 by means of fluid line 15. The position of the valve 10 is electrically controlled by a valve controller 30.

When a patient wearing the nasal cannula inhales during normal breathing, gas pressure in the cannula drops below ambient air pressure. This negative pressure is transmitted from port 10a through the valve and through fluid line 15 to the pressure sensor 20. Upon sensing a negative pressure event, the pressure sensor 20 causes the valve controller 30 to selectively connect port 10a to port 10c. In this "flow-on" position, the valve 10 allows NO gas to flow into the nasal cannula, from which the NO gas is delivered into one, or both, of the patient's nostrils.

The valve controller 30 maintains the valve in the "flow-on" position for a predetermined "pulse" time. At the end of the pulse time, the valve controller 30 returns the valve to the "flow-off" position (port 10a connected to port 10b), thereby completing a pulsed dose cycle. With the valve returned to the "flow-off" position, the device is ready for detection of the patient's next breath, and repetition of the pulsed dose cycle.

The pressure sensor 20 includes suitable means for sensing a negative fluidic pressure applied along line 15 and for generating an electrical signal upon sensing a negative pressure event. Suitable means for sensing a negative pressure associated with normal breathing include a pressure-to-electric (P/E) switch, which can be used in conjunction with a fluid amplifier. In some embodiments, the pressure sensor 20 includes a pressure transducer, e.g., a solid state-type, a capacitance-type, or an diaphragm-type (electromechanical) transducer.

Suitable valves, pressure sensing devices, valve controlling devices, and their integrated use for pulsatile delivery of a gas (oxygen) to a patient are described in detail in Durkan et al., U.S. Pat. No. 4,462,398. Prior art teachings with regard to devices for pulsatile delivery of oxygen through a nasal cannula are generally applicable in the present invention, except for possible material compatibility considerations. Materials compatible with NO include Teflon®, silicone, nickel, aluminum, and stainless steel. In addition, high pressure rubber hoses and plastic tubing commonly used for oxygen delivery are suitable for use with the NO concentrations used clinically.

The monitor 50 measures the flow-off time, i.e., the time during which port 10a of the valve 10 is connected to port 10b of the valve 10. When the valve 10 remains in the flow-off position for a predetermined time limit, the monitor 50 electrically signals the valve controller 30 to switch the valve 10 to the flow-on position (i.e., port 10a connected to port 10c) for a predetermined "purge" time. At the end of the predetermined purge time, the valve controller 30 switches the valve 10 back to the flow-off position, thus completing a purge cycle.

As long as the mixture of NO and nitrogen is flowing from the source and through the system, air is prevented from backing up into the nasal cannula. During the flow-off time, air begins mixing with residual NO in the nasal cannula. Oxygen in the air spontaneously reacts with the residual NO in the lines to produce $NO_2$, which is toxic. Thus, when the flow-off time reaches a predetermined limit, the monitor 50 electrically signals the valve controller 30 to switch the valve 10 to the flow-on position. This causes a predetermined amount of gaseous NO/nitrogen ("purge volume") to flow from the source (gas cylinder) and through the system, thereby purging accumulated $NO_2$ from the valve 10, the cannula, and any lines between the valve 10 and the cannula.

Preferably, the purge volume is between 1 and 5 dead space volumes. More preferably, the purge volume is between 2 and 4 dead space volumes, with about 3 dead space volumes being most preferred. The dead space volume is the total volume in the fluid path between port 10b and the ends of the nasal prongs, which terminate the nasal cannula. The dead space volume can be calculated readily from the internal dimensions of the components of the fluid pathway. The flow rate of the gaseous mixture of NO/nitrogen will be adjustable and known in terms of volume per unit time. Using this information, the desired purge volume can be converted to the predetermined purge time incorporated in a purge cycle.

In the embodiment represented by FIG. 1, the monitor measures the flow-off time indirectly, by means of electrical connections with the valve controller 30. In other embodiments, the monitor measures the duration indirectly, by means of electrical signals from the pressure sensor 20. In yet other embodiments, the monitor measures the duration directly, by means of a connection (electrical or mechanical) with the valve 10.

In the embodiment depicted in FIG. 1, the valve controller 30 controls the position of the valve 10. The valve controller 30 provides an input to the monitor 50 that indicates whether the valve 10 is in the "flow-off" position 10b (logical 1 or high voltage) or the "flow-on" position 10c (logical 0 or low voltage). The monitor 50 can employ a variety of methods to control the valve controller 30 and the alarm 40. These methods include microprocessor circuitry or TTL compatible circuitry. As an example, a monitor 50 that employs a combination of FETs and analog devices is described.

Figure 2:
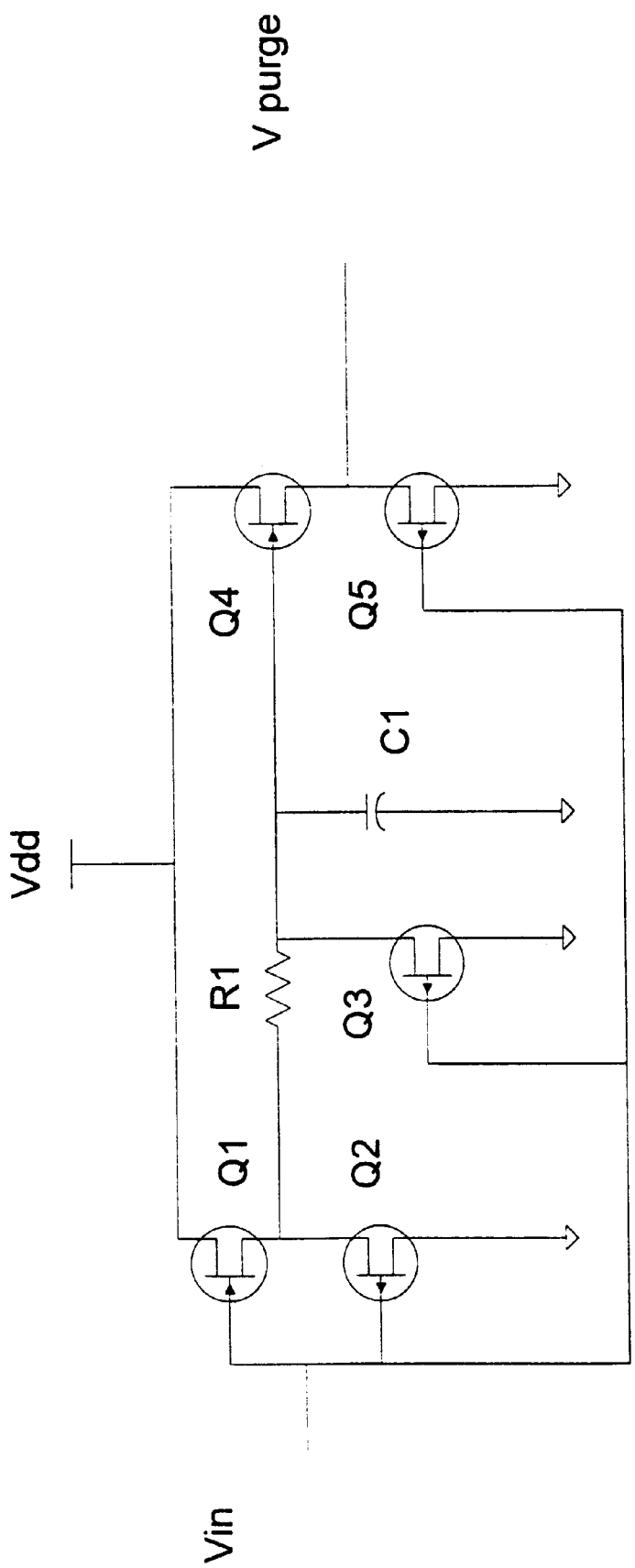
FIG. 2 is a schematic diagram of a purge timing circuit useful in a device according to the invention.

Referring to FIG. 2, a purge timing circuit has an input Vin that represents the flow-off and flow-on positions of the valve 10. When the valve is in the flow-off position, Vin transitions to a high voltage. Previous to the transition, the P-channel FETs (Q2, Q3, and Q5) were conductive, i.e., on, and the N-channel FET Q1 was not conductive, i.e., off. When the valve position changes and Vin transitions from a low to a high voltage, the P-channel FETs are turned off and the N-channel FET Q1 is turned on. Thus, the circuit is no longer clamped to ground. Current begins to flow from Vdd through Q1 and through the RC circuit formed by R1 and C1. After a time delay defined by the RC time constant, the voltage at the gate of Q4 is sufficient to turn Q4 on. At this time, current flows from Vdd through Q4 and Vpurge goes high.

When Vpurge is high, the valve controller 30 changes the position of the valve 10 to the flow-on position and purges the system. Consequently, the value of Vin transitions back to "0". The P-channel FETs Q2, Q3 and Q5 are on and the N-channel FET Q1 is off. Because the circuit is clamped to ground, the N-channel FET Q4 also is off and Vpurge returns to a "0".

The parameters of the purge timing circuitry are chosen to produce a transition at Vpurge after a predetermined time delay. For example, Vdd is 5 V; the threshold voltages of Q1, Q2, Q3, and Q5 are relatively low, e.g., 1 V; the threshold voltage of Q4 is higher, e.g., 4.5 V; and the RC time constant of R1 and C1 is designed to be approximately 15 seconds. Therefore, Q4 will turn on after approximately 15 seconds because the threshold voltage is chosen to be 90% of the supply voltage Vdd. If Vin is not high for 15 seconds or more, the P-channel FETs Q2, Q3, and Q5 reset the circuit by clamping the circuit to ground and discharging the capacitor.

Figure 3:
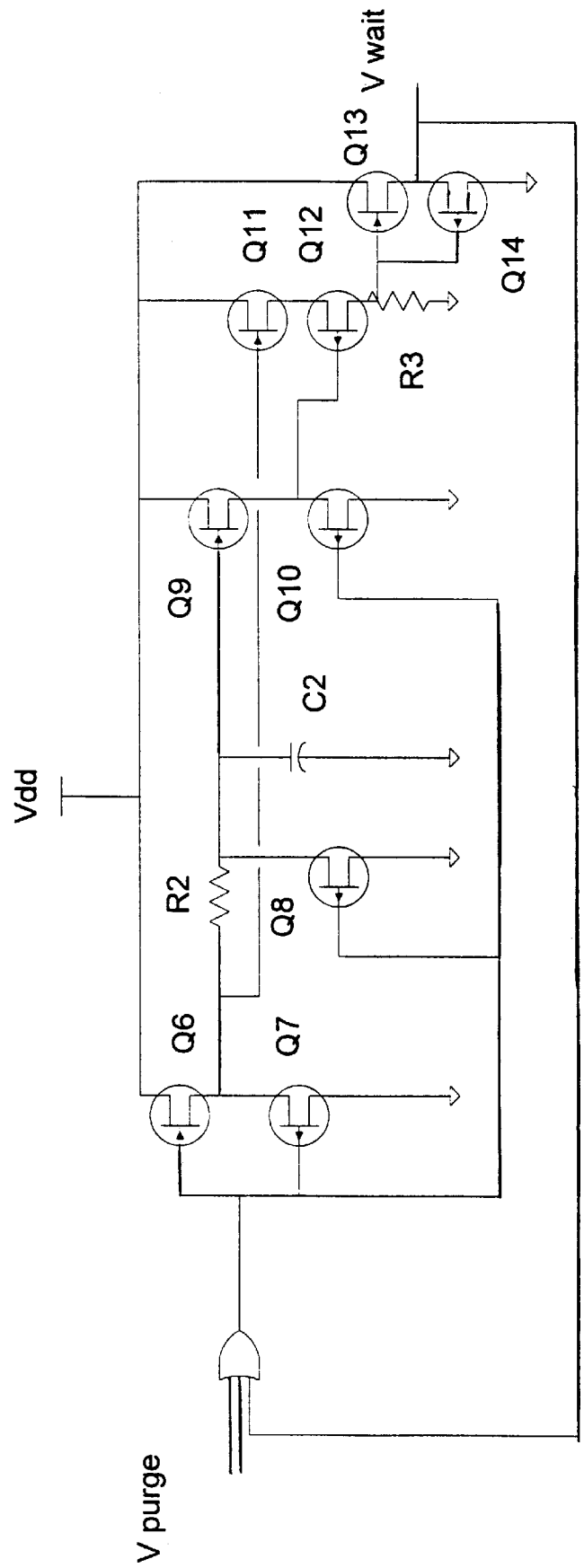
FIG. 3 is a schematic diagram of purge delay circuitry useful in a device according to the invention.

Referring to the purge delay circuitry of FIG. 3, when Vpurge is high, the signal Vwait goes high and provides a signal to the valve controller that the system should purge NO in the lines. The valve 10 moves to the "flow-on" position and NO flows through the system. The valve 10 (FIG. 1) remains in the flow-on position until Vwait, a pulse of predetermined duration, transitions back to a low state. The purge is also initiated on system startup by a power-on pulse which is the second input in the three input OR gate. The power on pulse is generated only once by a trigger device, known in the prior art, and ensures that fresh NO is available at start up.

The purge delay circuitry has an RC delay formed by R2 and C2 similar to the purge timing circuitry. The RC delay is designed to extend the Vwait pulse for the period required to purge 1 to 5 dead volumes of NO.

When Vpurge goes high, P-channel FETs Q7, Q8 and Q10 turn off and N-channel FET Q8 turns on. C2 begins to charge, and the drain of Q6 is connected to the gate of Q11. Therefore, N-channel FET Q9 is off; P-channel FET Q12 is on; and the combination of Q11 and Q12 conducts current to the gate of N-channel FET Q13. Because P-channel FET Q14 is off, the voltage at Vwait transitions to Vdd. Thus, the output transitions high almost instantaneously.

Vwait is fed back into the three input OR gate and holds the input to the gates of Q6 and Q7 at a high level. Thus, when valve 10 moves to the flow-on position and Vpurge transitions back to low, Vwait will remain high, and the RC circuit will continue to charge capacitor C2. When the capacitor is charged after a period defined by the RC delay of the circuit, Q9 turns on, and the gate of Q12 is high. Thus, Q12, a P-channel FET, stops conducting and the gates of Q13 and Q14 are low. When the gates are at a low voltage, Q13 is off and Q14 clamps Vwait to ground. When the pulse Vwait terminates, the valve controller 30 changes the valve position, and the purge timing circuitry again begins to monitor for pressure changes.

Similar to the purge timing circuitry, Q6, Q7, Q8 and Q10 of the purge wait circuitry have relatively low threshold voltages, e.g., 1 V, and Q9 has a threshold voltage approximately 90% of Vdd. Resistor R3 is a small resistor that ensures the full value of Vdd is applied to the gates of Q13 and Q14.

The monitor 50 is electrically connected to an alarm 40, which indicates when the predetermined flow-off time limit has been reached. A flow-off time in excess of the predetermined limit can result from various causes. For example, the nasal cannula may become dislodged from the patient's nostrils when the patient moves his/her head while asleep. The alarm 40 includes a visual indication such as a flashing light, or an audible indication such as a beeping tone, or both. The alarm alerts the patient or caretaker(s), so that the condition causing cessation of pulsed NO delivery can be promptly corrected. Prompt correction is particularly important where an NO rebound effect is a concern. NO rebound effects include pulmonary hypertension, hypoxemia, and heart failure.

Figure 4:
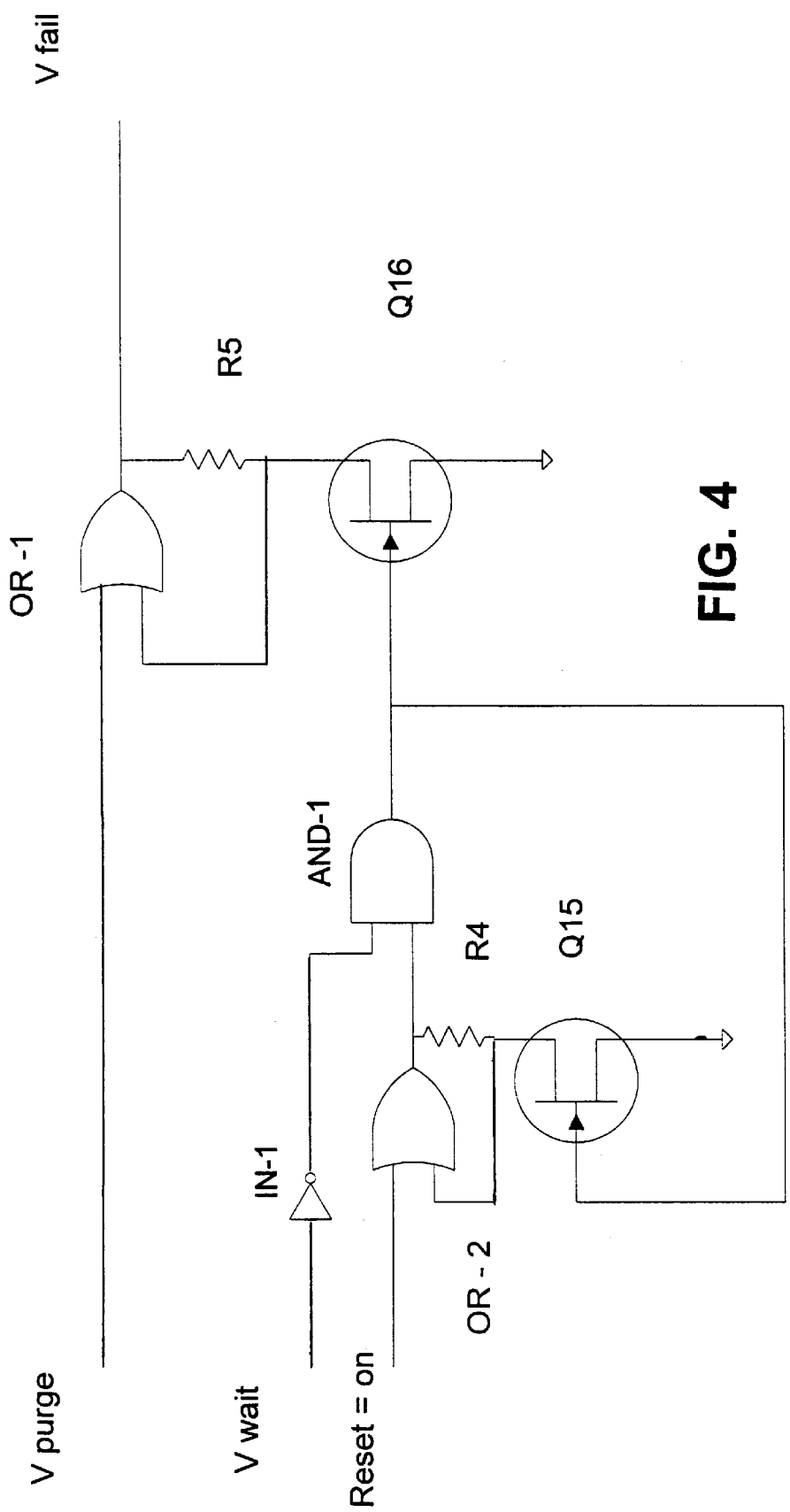
FIG. 4 is a schematic diagram of alarm circuitry useful in a device according to the invention.

Several alarm configurations can be constructed from the circuitry in FIGS. 2–4. For example, the output Vpurge can be connected to a "Wait" light (FIG. 5) to indicate the system is purging. The complement of Vwait can be connected to a "Ready" light to indicate the system has completed purging. Referring to FIG. 4, the reset logic is used for an embodiment of the invention where the patient, or other person, must reset a "Fail" (FIG. 5) light when a purge is performed. The output Vpurge is the input into an OR gate OR-1. The output of OR-1 is fed back as the second input to maintain the output Vfail in a high state. Vfail is connected to a "Fail" light (not shown) which is illuminated when Vfail is high. N-channel FET Q16 resets OR-1 when AND-1 provides a low output to the gate of Q16. With Vpurge low, Q16 causes the second input to OR-1 to go low, causing Vfail to go low.

However, Vfail does not transition to the low state until the purge cycle is complete (Vwait is low) and the patient resets the fail light (Reset=on). These signals are ANDed in AND-1 to detect this state. The output of AND-1 is used to reset the feedback of OR-1 and OR-2. Because Vpurge will transition to a low state before Vwait, Vfail will transition low when the feed back loop is clamped to ground.

OR-2 has a feedback loop to ensure that, if the fail reset is pressed before the purge cycle is complete, the fail light will extinguish when Vwait transitions to a low state. With AND-1 at a low state, N-channel FET Q15 will be off, which keeps OR-2 high. AND-1 will remain at a logic low state until Vwait goes low. When AND-1 goes high, the OR-2 and OR-1 gates are reset. The resistors R4 and R5 are small resistors that prevent the clamping FETs Q15 and Q16 from shorting Vdd to ground and that ensure the input is clamped to ground quickly. The circuitry does not generate a fail light on start up when the system initially purges, but does generate a wait light on start up based on Vwait.

Preferred embodiments of the invention include a purge cycle indicator, which is activated at the beginning of every purge cycle and deactivated at the end of the purge cycle. The indicator can be visual, audible, or both. The purge indicator can be a readily visible, color-coded light or a liquid crystal display. Suitable markings for a light that illuminates during the purge cycle include "WAIT" and "PURGING." Suitable purge-cycle messages for a liquid crystal display include "WAIT" and "PURGING." Upon completion of the purge cycle, suitable liquid crystal display messages include "OK" and "READY."

Preferred embodiments of the invention include automatic purging each time the device is connected to a power source after having been disconnected. Connection and disconnection can be by means of an ordinary on/off switch, by battery insertion and removal, or by plugging and unplugging a power cord. Preferably, a purge cycle (discussed above) is triggered whenever an electrical circuit in the valve controller 30 energized after having been de-energized.

Typically, the source of gaseous NO/nitrogen used for inhaled NO therapy is a high pressure cylinder, which requires an appropriate (pin index safety system or diameter index safety system) pressure regulator. A device according to this invention can be incorporated into an integrated unit that includes a pressure regulator. Alternatively, the device can be a separate unit connected between a conventional NO pressure regulator and a conventional nasal cannula.

The device of this invention can be used in conjunction with a conventional flow regulator. Referring to FIG. 1, the flow regulator (not shown) is inserted at a point in the fluid path between a pressure regulator (not shown) and port 10c on the valve 10.

Referring to FIG. 1, the NO dosage delivered to the patient by the device of this invention can be adjusted in any of at least three ways. One way of adjusting the dosage is varying the pulse time, i.e., the time that the valve 10 is in the flow-on position during a pulsed dose cycle, wherein the flow rate remains constant. A second way of adjusting the dosage is varying NO/nitrogen flow rate, wherein the pulse time remains constant. Flow rate can be adjusted by any suitable means, e.g., a manual valve or a proportioning solenoid. A third way of adjusting the dosage is programming the valve controller 30 to move the valve 10 to the flow-on position on a breath-dependent schedule, e.g., every second breath, every third breath, or every fourth breath.

In therapeutic use of a device of this invention, the desired NO dosage will be determined in accordance with accepted medical practice, depending on the condition being treated and the status of the patient. Regardless of the means for adjusting NO dosage, the NO/nitrogen flow rate during the flow-on phase of the pulsed dose cycle is preferably from 0.25 to 8 liters per minute, and more preferably from 1 to 4 liters per minute.

The following equations are useful for obtaining the desired NO dosage when delivering inhaled NO through a nasal cannula system:

$$[NO]=(NO\ flow \times source\ ppm)/total\ flow$$

$$[NO]in\ cannula=(desired\ NO\ dose \times mean\ inspiratory\ flow)/cannula\ flow$$

For additional guidance concerning calculations and considerations for inhaled NO delivery systems, see Hess et al., 1997, *Resp. Care Clinics of North America* 3:371.

Figure 5:
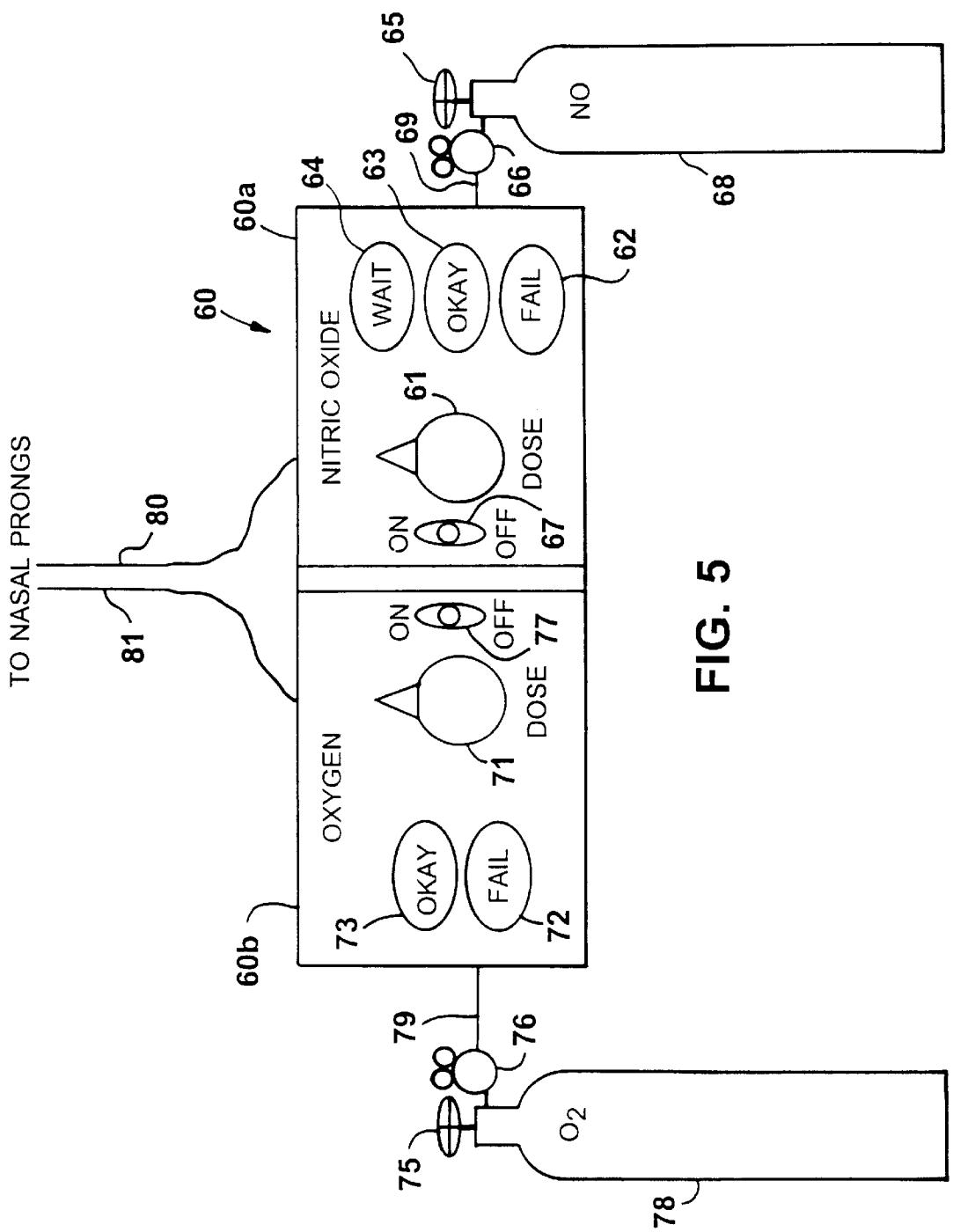
FIG. 5 is a schematic representation of a device for separate, concurrent, pulsed delivery of inhaled NO through a split cannula system to a spontaneously breathing patient.

FIG. 5 illustrates selected features of a device 60 for separate, concurrent, pulsed delivery of inhaled nitric oxide and pulsed delivery of oxygen through a split nasal cannula 80, 81 to a spontaneously breathing patient.

A mixture of NO/nitric oxide flows from an NO source cylinder 68 through a cylinder shutoff valve 65, a pressure regulator 66, and fluid line 69, into the device 60. The NO control panel 60a includes an NO main power switch 67 and a knob 61 for adjusting NO dosage to the desired level. The NO control panel 60a also includes a purge cycle indicator light 64, an indicator light that signals when it is safe for the patient to begin using the device 63, and an alarm indicator light 62.

Oxygen flows from an oxygen source cylinder 78 through a cylinder shutoff valve 75, a pressure regulator 76, and fluid line 79, into the device 60. The oxygen control panel 60b includes an oxygen main power switch 77 and a knob 71 for adjusting oxygen dosage to the desired level. The oxygen control panel 60b includes a first light 73, which indicates that pulsed oxygen delivery is proceeding without the oxygen flow-off time exceeding the predetermined limit. The oxygen control panel 60b also includes a second light 72, which indicates that pulsed oxygen delivery has failed to occur without exceeding the predetermined flow-off time.

Other embodiments are within the following claims.

We claim:

1. A nitric oxide pulse delivery device for delivering nitric oxide to a spontaneously breathing patient, comprising:

a valve having a first, a second, and a third port, the first port being selectively communicable with the second port or the third port;

a pressure sensor in fluid communication with the third port;

a valve controller which is responsive to the pressure sensor, and which selectively connects the first port to the second port, said second port being connected to a source of nitric oxide gas, when a negative pressure event is sensed, maintains the connection for at least a portion of the negative pressure event duration, and reconnects the first port to the third port after a predetermined pulse time; and a monitor which is operably linked to the valve controller, and which measures the duration of connection between the first port and third port, and signals the valve controller to selectively connect the first port to the second port for a predetermined purge time when the duration of connection between the first port and third port exceeds a predetermined flow-off time, and then signals the valve controller to reconnect the first port to the third port.

2. The device of claim 1, further comprising a means for inactivating the device when not in use, and a means for triggering the valve controller to selectively connect the first port to the second port for a predetermined purge time whenever the device undergoes start-up following a state of inactivation.

3. The device of claim 1, wherein the purge time is preselected so as to provide a purge volume of 1 to 5 dead space volumes, a dead space volume being the volume in the fluid path between the third port and the ends of nasal prongs connected to the first port.

4. The device of claim 3, wherein the purge volume is from 2 to 4 dead space volumes, a dead space volume being the volume in the fluid path between the third port and the ends of nasal prongs connected to the first port.

5. The device of claim 1, further comprising an alarm which is operably connected to the monitor, and which provides a visual or audible indication whenever the duriation of connection between the first port and third port exceeds a predetermined flow-off time.

6. The device of claim 1, further comprising a purge cycle indicator that provides a continuous visual or audible indication that begins whenever a purge cycle begins, continues throughout the purge cycle, and ends when the purge cycle ends.

7. A nitric oxide pulse delivery and oxygen pulse delivery device for separately and concurrently delivering nitric oxide and oxygen through a split nasal cannula to a spontaneously breathing patient, comprising:

a pulsed nitric oxide delivery system comprising:

a valve having a first, a second, and a third port, the first port being selectively communicable with the second port or the third port;

pressure sensor in fluid communication with the third port;

a valve controller which is responsive to the pressure sensor, and which selectively connects the first port to the second port, said second port being connected to a source of nitric oxide gas, when a negative pressure event is sensed, maintains the connection for at least a portion of the negative pressure event duration, and reconnects the first port to the third port after a predetermined nitric oxide pulse time; and a monitor which is operably linked to the valve controller, and which measures the duration of connection between the first port and third port, and signals the valve controller to selectively connect the first port to the second port for a predetermined purge time when the duration of connection between the first port and third port exceeds a predetermined flow-off time, and then signals the valve controller to reconnect the first port to the third port; and a pulsed oxygen delivery system comprising:

a valve having a first, a second, and a third port, the first port being selectively communicable with the second port or the third port;

a pressure sensor in fluid communication with the third port; and a valve controller which is responsive to the pressure sensor, and which selectively connects the first port to the to the second port when a negative pressure event is sense, maintains the connection for at least a portion of the negative pressure event duration, and reconnects the first port to the third port after a predetermined oxygen pulse time.

8. The device of claim 7, further comprising an alarm system comprising:

a monitor operably linked to the valve controller, which monitor measures the duration of connection between the first port and third port; and an alarm indicator operably linked to the monitor so that an alarm indication results when the monitor detects a duration of connection between the first port and third port equal to, or greater than a predetermined time limit.

* * * * *

UNITED STATES PATENT AND TRADEMARK OFFICE
CERTIFICATE OF CORRECTION

PATENT NO. : 6,142,147
DATED : November 7, 2000
INVENTOR(S) : C. Alvin Head and Dean R. Hess It is certified that error appears in the above-identified patent and that said Letters Patent is hereby corrected as shown below:

Column 1, Page 2,
Kerby et al., after *Chest*, delete [379-372] and insert -- 369-372 --.

Signed and Sealed this

Twenty-eighth Day of August, 2001

Attest:

*Nicholas P. Godici*

NICHOLAS P. GODICI
*Attesting Officer*     *Acting Director of the United States Patent and Trademark Office*